United States Patent [19]

Summers

[11] Patent Number: 4,816,456
[45] Date of Patent: Mar. 28, 1989

[54] ADMINISTRATION OF MONOAMINE ACRIDINES IN CHOLINERGIC NEURONAL DEFICIT STATES

[76] Inventor: William K. Summers, 624 W. Duarte Rd., Suite 101, Arcadia, Calif. 91006

[21] Appl. No.: 98,871

[22] Filed: Sep. 24, 1987

Related U.S. Application Data

[63] Continuation-in-part of Ser. No. 914,076, Oct. 1, 1986, abandoned.

[51] Int. Cl.⁴ .................. A61K 31/44; A61K 31/495; C07D 401/00; C07D 265/36
[52] U.S. Cl. .................................. 514/255; 514/297; 544/361; 546/105
[58] Field of Search ................. 514/255, 297; 544/361; 546/105

[56] References Cited

U.S. PATENT DOCUMENTS

| | | | |
|---|---|---|---|
| 1,629,873 | 5/1927 | Jensch | 546/105 |
| 2,083,903 | 6/1937 | Hata et al. | 544/361 |
| 3,043,842 | 7/1962 | Craig et al. | 544/361 |
| 3,489,837 | 1/1970 | Hyman et al. | 514/297 |
| 4,631,286 | 12/1986 | Shulstse et al. | 514/297 |

FOREIGN PATENT DOCUMENTS 0179383 4/1986 European Pat. Off. .

OTHER PUBLICATIONS

Davis et al, "Selective Loss of Central Cholinergic Neurons in Alzheimer's Disease", *Lancet* (1980), vol. 2, p. 1403.

Harbaugh, M. D. et al, "Preliminary Report: Intracranial Cholinergic Drug Infusion in Patients with Alzheimer's Disease", *Neurosurgery* (1984), vol. 15, pp. 494–496.

Summers, W. K. et al, "THA—A Review of the Literature and Its Use in Treatment of Five Overdose Patients", *Clinical Toxicology* (1980), vol. 16, pp. 269–281.

Summers, W. K. et al, "Use of THA in Treatment of Alzheimer-Like Dementia: Pilot Study in Twelve Patients", *Biological Psychiatry* (1981), vol. 16, No. 2, pp. 145–153.

Kaye, W. H. et al, "Modest Facilitation of Memory in Dementia with Combined Lecithin and Anti-Cholinerestase (SR) Treatment", *Biological Psychiatry* (1982), vol. 17, No. 2, pp. 275–280.

Thal, L. J. et al, "Oral Physostigmine and Lecithin Improve Memory in Alzheimer's Disease", *Annals of Neurology* (1983), vol. 13, No. 5, pp. 491–496.

Soni, N. et al., "4-Aminopyridine—A Review", *Anesthesia and Intensive Care* (1982), vol. 10, pp. 120–126.

*Primary Examiner*—Stanley J. Friedman
*Attorney, Agent, or Firm*—Burns, Doane, Swecker & Mathis

[57] ABSTRACT

A method for treating central nervous system or peripheral nervous system cholinergic deficit states such as Alzheimer's disease in a mammal, said method comprising administering to said mammal an amount of a monoamine acridine derivative effective in the treatment of a cholinergic deficit state and for a time sufficient to achieve a suitable blood level to treat said cholinergic deficit state. The preferred monoamine acridine derivative is 1,2,3,4-tetrahydro-5-aminoacridine. A unit dosage pharmaceutical composition of matter comprising an effective amount of said monoamine acridine derivative sufficient to treat said cholinergic deficit state and a pharmaceutically acceptable inert carrier therefor is also disclosed.

38 Claims, 6 Drawing Sheets

ADMINISTRATION OF MONOAMINE ACRIDINES IN CHOLINERGIC NEURONAL DEFICIT STATES

CROSS REFERENCE TO RELATED APPLICATIONS

This application is a continuation-in-part of U.S. Ser. No. 914,076, filed Oct. 1, 1986 now abandoned.

BACKGROUND OF THE INVENTION

The present invention relates to a method for treating central nervous system and peripheral nervous system cholinergic deficit states. It also relates to novel compositions of matter for treating such disease states. More particularly, the present invention relates to the use of monoamine acridine derivatives in the treatment of such states.

A wide variety of recognized diseases fall within the ambit of cholinergic deficit states. At the present time, Alzheimer's disease has gained the most attention. In 1907 Alois Alzheimer described a 51 year-old woman with a progressive dementia leading to death within approximately four and one-half years. At autopsy, the woman's brain was grossly atrophic. Microscopic examination of the brain revealed diffuse neurofibrillary degenerative change with numerous miliary foci (senile plaque). The dementia described has been given several names, including Alzheimer's disease, Senile Dementia of the Alzheimer's type, PreSenile Dementia and Primary Degenerative Dementia. It is now recognized as one of our major health care problems. The disease is a progressive deterioration of the brain resulting in memory loss, cognitive deficits, and altered behavior. The prevalence of the disease is not clearly established and estimates vary from 10 to 15 percent of the population over age 65. The major brunt of the disease is in the eighth and ninth decades, and this is the segment of the population increasing most rapidly in number. Alzheimer's disease is estimated to affect 1.5 to 3.0 million people in the United States alone at the present time. Thus, Alzheimer's disease is a major health problem and is reported to be the fifth most common cause of death in the United States. With advances in medical care, the survival rate of patients with dementia has been increasing. So the increaase in the size of the at risk population and its survival makes the search for solutions a high priority. In addition, the cost of nursing home rates alone is staggering.

It is now recognized that Alzheimer's disease may occur at virtually any age. The precise cause of the illness is unknown. A variety of non-specific treatments have been proposed which rely on the theory that the cause of the disease is cerebral atherosclerosis. Such treatments include the use of cerebral vasodilators, vitamins, chelating agents, hyperbaric oxygen, precursor amino acids and vasopressin. However, there is no convincing evidence that any of the foregoing are beneficial.

In 1976, the neurochemical deficit of Alzheimer's Disease became partially defined by Davies et al, "Selective Loss of Central Cholinergic Neurons in Alzheimer's Disease", *Lancet* (1980), vol. 2, p. 1403. Numerous investigators have demonstrated a reduction in the enzyme choline acetyltransferase in autopsy material from Alzheimer's patients versus agematched controls. It has been determined that there is an additional moderate reduction of both true and "pseudo" acetylcholinesterase (AChE and BuChE). Post synaptic muscarinic receptors are generally intact. In addition, direct correlation of memory deficits seen in Alzheimer's disease patients to the post-mortem choline acetyltransferase levels has been established. Recent evidence suggests that the most important specific locus of cholinergic neurons in the central nervous system of patients with Alzheimer's disease is the nucleus basalis and the diagonal band of Broca.

At the present time, there are three possible approaches to enhance cholinergic transmission in the central nervous system. The first approach is to enhance cholinergic neurons by excessive exposure to a form of choline. Such attempts have been mildly successful but only in the early stages of Alzheimer's disease.

The second approach involves post synaptic direct stimulation of muscarinic receptors by oral or intravenous administration of drugs. No reports of this approach appear in the literature. This is likely because such direct stimulation by agents such as oxotremorine, muscarine and pilocarpine would be expected to have a low therapeutic index, i.e., a high effective dose to toxic dose ratio. In addition, a variety of undesirable, non-specific side efects would be expected. One agent, bethanechol chloride, a post synaptic, muscarinic agonist has been administered intrathecally with limited success on four patients by Harbaugh, R. E. et al and reported in "Preliminary Report: Intracranial Cholinergic Drug Infusion in Patients with Alzheimer's Disease", *Neurosurgery* (1984), vol. 15, pp. 514–518. This method of administration was fraught with problems since it requires the heroics of neurosurgery. Further, bethanechol chloride itself is not the ideal agent since it is a quaternary ammonium compound and thus has limited penetration of the blood-brain barrier.

The third approach to enhance cholinergic transmission involves the inhibition of acetylcholinesterase, the enzyme that metabolizes acetylcholine. In this approach a reversible carbamate inhibitor such as physostigmine may be used. The most obvious disadvantage associated with this approach is that the short half-life of these drugs requires a frequency of administration of approximately every two to four hours as noted by Thal, L. J. et al, "Oral Physostigmine and Lecithin Improve Memory in Alzheimer's Disease", *Annals of Neurology* (1983), vol. 13, no. 5, pp. 491–496. The reversible carbamate inhibitors also have a low therapeutic index. Thus, even the inhibition of acetylcholinesterase does not appear to offer a practical solution for chronic cholinergic deficit states such as Alzheimer's disease.

Yet another class of pharmacological agents exist which enhance the cholinergic system through synaptic inhibition of acetylcholinesterase. One member of this claim is 1,2,3,4-tetrahydro-5-aminoacridine (THA), reported by Summers, W. K. et al, "THA—A Review of the Literature and Its Use in Treatment of Five Overdose Patients", *Clinical Toxicology* (1980), vol. 16, pp. 269–281. When 1,2,3,4-tetrahydro-5-aminoacridine was first explored in the late 1940's, it was determined that it was a potent anticholinesterase that reversed morphine narcosis, reversed barbiturate narcosis, reversed magnesium chloride induced coma, and prevented ventricular fibrillation precipitated by digitalis or electric shock.

In 1979 the use of intravenous 1,2,3,4-tetrahydro-5-aminoacridine on patients with Alzheimer's disease was reported by Summers, W. K. et al, "Use of THA in Treatment of Alzheimer-Like Dementia: Pilot Study in Twelve Patients", *Biological Psychiatry* (1981), vol. 16, no. 2, pp. 145–153. This study tested the cholinergic hypothesis of organic brain syndromes, in general, and of Alzheimer's disease, in particular. Approximately 75% of the patients showed improvement in the global sense. However, in practical terms, this study did not provide a treatment for Alzheimer's disease. Giving medications acutely (suddenly not chronically) and intravenously is not a solution for a chronic disorder such as Alzheimer's disease which oftentimes follows a course of eight years from onset to death.

Kaye, W. H. et al, "Modest Facilation of Memory in Dementia with Combined Lecithin and Anticholinerestase Treatment", *Biological Psychiatry* (1982), vol. 17, no. 2, pp. 275–280 reported that only a modest improvement in memory could be obtained by use of oral 1,2,3,4-tetrahydro-5-aminoacridine. Kaye et al tested the use of 30 mg of 1,2,3,4-tetrahydro-5-aminoacridine (THA) and/or 60 grams of lecithin on ten patients. Both the 30 mg of THA and the 60 grams of lecithin were divided into three doses and administered to each patient at 10:00 pm and then the next day at 8:00 am and noon. The patients were then tested at 2:00 pm. Four trials of drug administration were conducted on each patient. A minimum of 56 hours elapsed between trials. The four trials involved both lecithin placebo and THA placebo; active lecithin and lecithin placebo; and active THA and active lecithin. No dosage variation was tested. The results of the study were not promising. Although the less impaired patients increased the number of words remembered on serial learning testing with the combined 1,2,3,4-tetrahydro-5-aminoacridine/lecithin therapy, the combined therapy did not restore any patient to normal functioning. Neither lecithin nor 1,2,3,4-tetrahydro-5-aminoacridine alone produced improvement in memory function in any of the patients. Thus, researchers in this field turned their attention to other treatment methods as evidenced by Harbaugh, R. E. et al, noted above, and Thal, L. J. et al, noted above.

Earlier work in this field also demonstrated that 4-aminopyridine was capable of reversing certain central anticholinergic states such as drug-induced coma. The mechanism of 4-aminopyridine is now believed to be due to post synaptic potassium channel blockade as described by Soni, N. et al, "4-Aminopyridine—A Review", *Anesthesia and Intensive Care* (1982), vol. 10, pp. 120–126. Thus, the search for a suitable treatment for Alzheimer's disease continues.

SUMMARY OF THE INVENTION

Surprisingly, contrary to the teachings of the prior art, the present inventor now finds that certain monoamine acridine derivatives can be orally administered to mammals, especially humans, in an amount effective for the treatment of central nervous system and peripheral nervous system cholinergic deficit states.

The present inventor has now discovered a method for treating central nervous system or peripheral nervous system cholinergic defict states in a mammal. The method comprises administering to a mammal an amount of a monoamine acridine derivative effective in the treatment of cholinergic defict states and for a time sufficient to achieve a suitable blood level to treat said cholinergic deficit state. The monoamine acridine derivative has the formula:

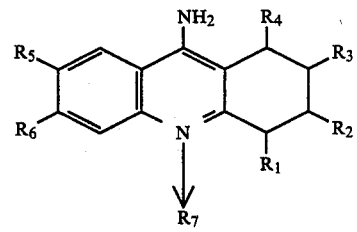

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy, or ethoxy; and $R_7$ represents no radical; an N-oxy radical; a $C_1$–$C_{20}$ alkyl radical or a radical selected from the group consisting of

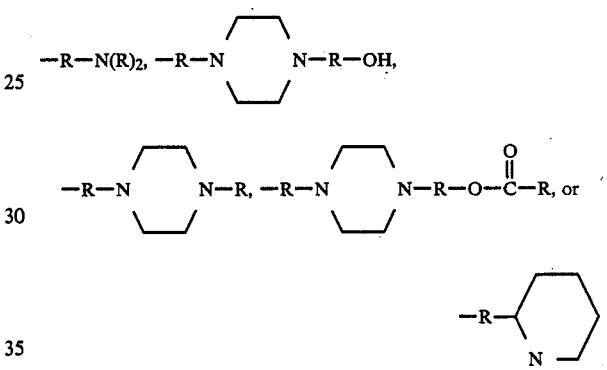

wherein each R is independently selected from $C_1$–$C_{20}$ alkyl; and pharmaceutically acceptable salts thereof. Each of the foregoing alkyl groups may be straight chain or branched.

The present inventor has also discovered a pharmaceutical composition of matter for treating said cholinergic deficit states in a mammalian organism in need of such treatment, said composition comprising a unit dosage amount of the monoamine acridine derivative described above suitable to treat said cholinergic deficit state and a pharmaceutically acceptable inert carrier therefor.

The compounds of the present invention have a wide number of advantages over the prior art methods of treating central nervous system cholinergic deficit states. They are effective, relatively non-toxic and suitable for long-term treatment. Suitable blood levels may be maintained when orally administered three to four times a day. Many current prior art treatments require a greater frequency of administsration. At the present time, there are no known drug-drug interactions between the subject monoamine acridine derivatives and the drugs currently used in the treatment of cholinergic deficit states. The monoamine acridine derivatives are readily absorbed after oral ingestion and no neurosurgical procedures or intravenous injections are necessary.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein.

DESCRIPTION OF THE PREFERRED EMBODIMENTS

Figure 1:
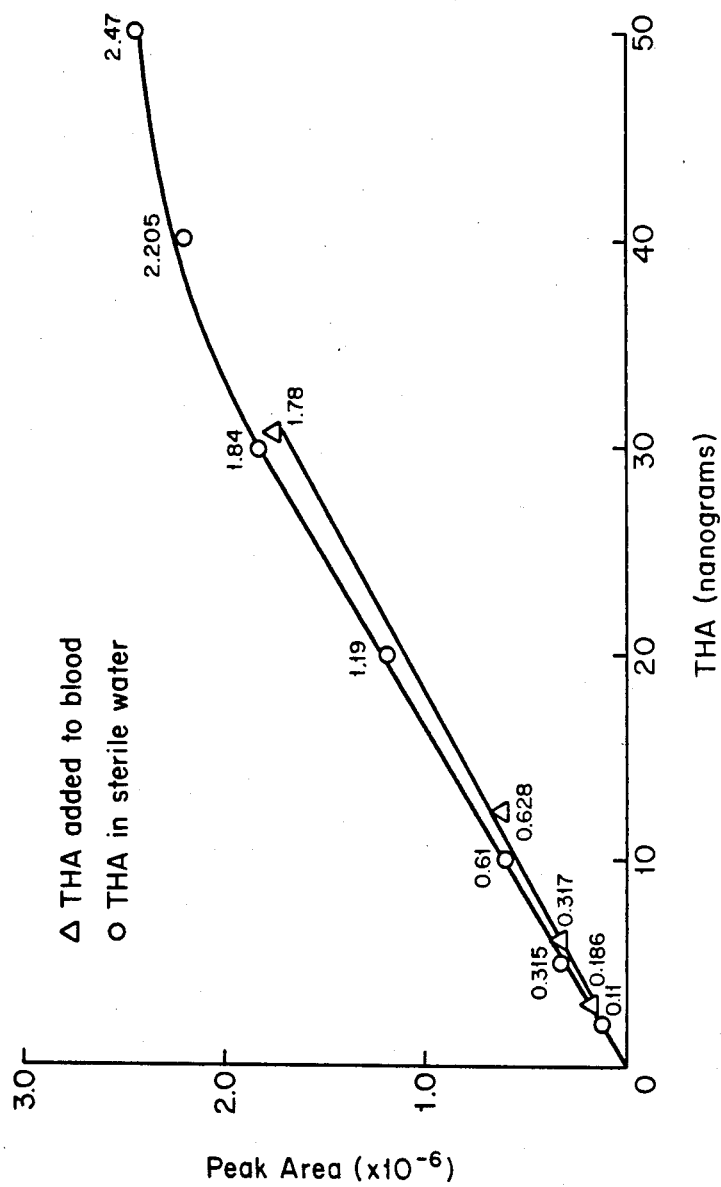
FIG. 1 shows the sensitivity of the serum 1,2,3,4-tetrahydro-5-aminoacridine assay over a range of zero to thirty mµg/ml.

The present invention is directed to a method of treating central nervous system or peripheral nervous system cholinergic deficit states in a mammal, said method comprising administering to said mammal an amount of a monoamine acridine derivative or pharmaceutically acceptable salt thereof effective in the treatment of cholinergic deficit states and for a time sufficient to achieve a suitable blood level to treat said cholinergic deficit state. Suitable monoamine acridine derivatives are described below:

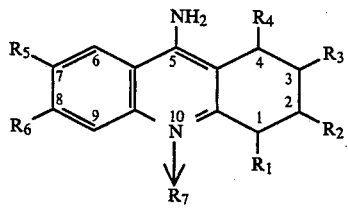

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$, and $R_4$ are all hydrogen; $R_5$ represents hydrogen, hydroxy, methoxy or ethoxy; $R_6$ represents hydrogen, hydroxy, methoxy or ethoxy; and $R_7$ represents no radical; an N-oxy radical; a $C_1$-$C_{20}$ alkyl radical or a radical selected from the group consisting of

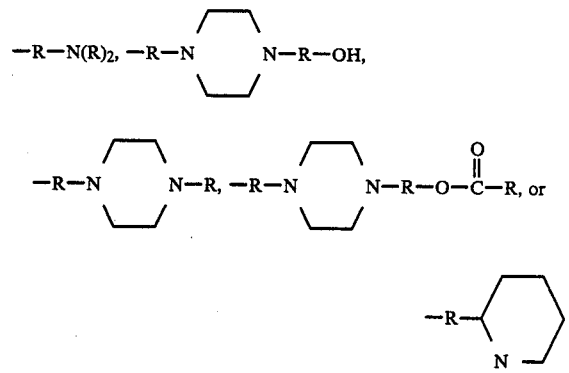

wherein each R is independently selected from $C_1$-$C_{20}$ alkyl; and pharmaceutically acceptable salts thereof. Each of the foregoing alkyl groups may be straight chain or branched.

Particularly preferred compounds intended for use in the practice of the present invention include 1,2,3,4-tetrahydro-5-aminoacridine (also referred to as THA) and derivatives thereof. Pharmaceutically acceptable salts are also included in this description. The chemical structure for 1,2,3,4-tetrahydro-5-aminoacridine is set forth below:

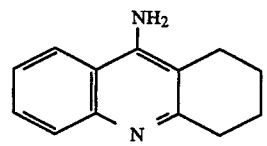

Typical derivatives of THA which are also useful in the practice of the present invention include the following:

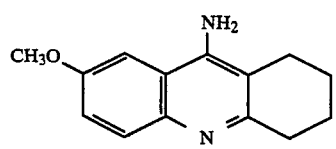

7-methoxy-1,2,3,4-tetrahydro-5-aminoacridine

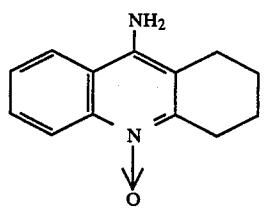

N-oxy-1,2,3,4-tetrahydro-5-aminoacridine

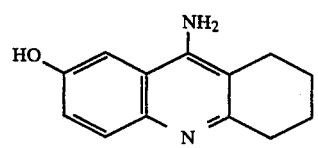

7-hydroxy-1,2,3,4-tetrahydro-5-aminoacridine

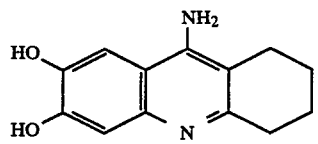

7,8-dihydroxy-1,2,3,4-tetrahydro-5-aminoacridine

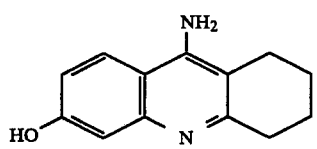

8-hydroxy-1,2,3,4-tetrahydro-5-aminoacridine

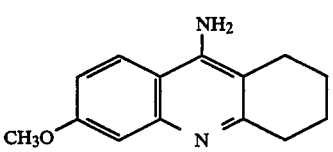

8-methoxy-1,2,3,4-tetrahydro-5-aminoacridine

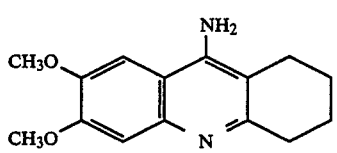

7,8-dimethoxy-1,2,3,4-tetrahydro-5-aminoacridine

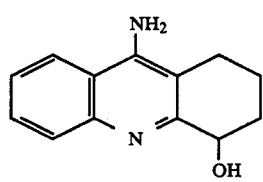

1-hydroxy-1,2,3,4-tetrahydro-5-aminoacridine

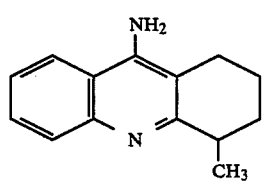

1-methyl-1,2,3,4-tetrahydro-5-aminoacridine

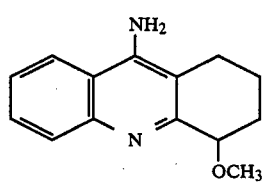

1-methoxy-1,2,3,4-tetrahydro-5-aminoacridine

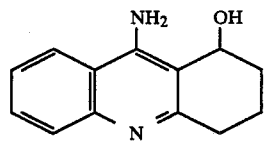

4-hydroxy-1,2,3,4-tetrahydro-5-aminoacridine

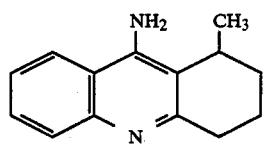

4-methyl-1,2,3,4-tetrahydro-5-aminoacridine

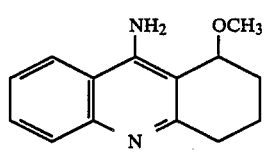

4-methoxy-1,2,3,4-tetrahydro-5-aminoacridine

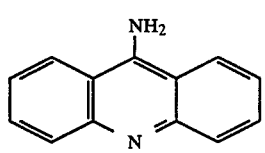

5-aminoacridine

The foregoing derivatives of 1,2,3,4-tetrahydro-5-aminoacridine are all believed to be active metabolites of 1,2,3,4-tetrahydro-5-aminoacridine. The preferred compound in the practice of the present invention is 1,2,3,4-tetrahydro-5-aminoacridine.

$R_7$ is preferably no radical, however, the following substituents are also preferred for $R_7$:

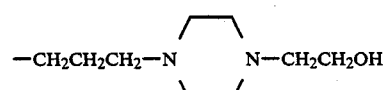

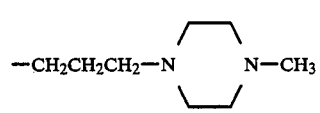

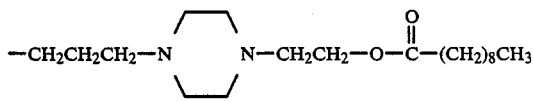

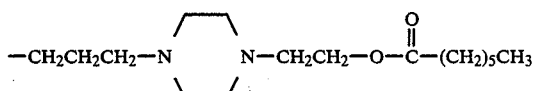

-continued

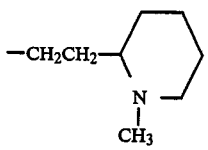

The foregoing preferred substituents for $R_7$ are preferably substituents on 1,2,3,4-tetrahydro-5-aminoacridine.

Any of the foregoing compounds may be prepared by processes known in the art. For instance, reference may be made to any standard chemical textbook for reaction processes and conditions.

The precise amount of monoamine acridine derivative for use in the present invention will vary depending, for example, on the specific drug chosen, the condition for which the drug is administered and the size and kind of the mammal. Generally speaking, the monoamine acridine derivative can be employed in any amount effective in the treatment of central nervous system or peripheral nervous system cholinergic deficit states. For certain disease states, the amount may be sufficient to substantially reverse symptoms of cholinergic deficit states. The symptoms of these states, including senile dementia of the Alzheimer's type, are improved.

For humans, typical effective amounts of monoamine acridine derivatives for use in the unit dose compositions of the present invention range from about 40 mg to about 1 gram per 24 hours depending on the monoamine acridine selected; however, greater amounts may be employed, if desired. This range is based on administration to a 70 kg human. A preferred amount is from about 100 mg to about 300 mg. The more preferred range contains about 100 mg to about 200 mg of the monoamine acridine derivative per 24 hours.

Preferred unit dose compositions for 1,2,3,4-tetrahydro-5-aminoacridine contain 40 mg, 50 mg, 75 mg, 100 mg, 150 mg or 200 mg per dose. The 75 mg, 100 mg, 150 mg and 200 mg unit dose compositions are preferably sustained release. The foregoing unit dose ranges are based on one dose per tablet, capsule, pill, 5 cc of elixir, 10 cc of suspension or the like. Other than the oral form of administration suitable dosage forms are those associated with the intramusclar, subcutaneous, rectal, topical, e.g., dermal, and the like routes of administration. Sustained release dosage forms are preferred. Thus, the compositions of this invention may be administered by pump or as a dermal patch or in an oil for injection. The only route of administration not suggested in the practice of the present invention is the intravenous route of administration since that route is generally only advantageous for acute treatment and is not considered advantageous for the treatment of a chronic disease state such as Alzheimer's where treatment is needed on a continuous basis.

As noted earlier, the preferred monoamine acridine derivative is 1,2,3,4-tetrahydro-5-aminoacridine. The blood 1,2,3,4-tetrahydro-5-aminoacridine concentration which is effective in the treatment of central nervous system and peripheral nervous system cholinergic deficit states is between about 5 and about 70 m$\mu$g/ml. A blood level in this range affords substantial improvement in Alzheimer's disease related symptoms. FIG. 1 shows the sensitivity of the serum 1,2,3,4-tetrahydro-5-aminoacridine assay over a range of zero to thirty m$\mu$g/ml. A serum level of about 5 to about 70 m$\mu$g/ml may be achieved by the oral administration of about 100 mg to about 200 mg of 1,2,3,4-tetrahydro-5-aminoacridine every six to eight hours. Thus, a daily dose of about 600 mg to about 1600 mg is preferred. The preferred blood concentrations of other monoamine acridine derivatives has not yet been determined. However, it should be noted that the frequency of administration will vary depending on the blood level desired and the specific monoamine acridine derivative selected. Thus, the monoamine acridine derivative may be administered, for instance, every two, four, six, eight, ten or twelve hours.

It is also possible to administer the monoamine acridine derivatives of the present invention in a time release formulation. A wide variety of methods are now available in the art for preparing time release or long-acting compositions. Any of these time release or long-acting formulations are suitable in the practice of the present invention as long as it does not adversely affect the effectiveness of the monoamine acridine derivative in the treatment of cholinergic deficit states. Advantages of time release formulations include a lower concentration of peak serum absorption which substantially reduces the adverse side effects and toxicity of the compound administered. In addition, a reduced frequency of administration results, which substantially improves patient compliance. A frequency of administration of every 12 or 24 hours would be preferred. In addition, a more constant serum concentration of the monoamine acridine derivative would result thereby allowing a more consistent relief of symptoms.

Any form of monoamino acridine derivative other than intravenous is suitable in the practice of the present invention. Typical dosage forms include tablets, capsules, pills, bulk powders, elixirs, solutions, suspensions, syrups, suppositories or ointments, creams and the like for topical administration.

Preferably, the monoamine acridine derivative is combined with any suitable nontoxic pharmaceutically acceptable inert carrier material. Such carrier materials are well known to those skilled in the art of pharmaceutical formulations. For those not skilled in the art, reference is made to the text entitled, "Remington's Pharmaceutical Sciences". In a typical preparation for oral administration, e.g., tablet or capsule, the monoamine acridine derivative in an effective amount for the treatment of central nervous system or peripheral nervous system cholinergic deficit states is combined with any oral nontoxic pharmaceutically acceptable inert carrier such as lactose, starch (pharmaceutical grade), dicalcium phosphate, calcium sulfate, kaolin, mannitol and powdered sugar. Additionally, when required, suitable binders, lubricants, disintegrating agents and coloring agents can also be included. Typical binders include starch, gelatin, sugars such as sucrose, molasses and lactose, natural and synthetic gums such as acacia, sodium alginate, extract of Irish moss, carboxymethylcellulose, methylcellulose, polyvinylpyrrolidone, polyethylene glycol, ethylcellulose and waxes. Typical lubricants for use in these dosage forms can include, without limitation, boric acid, sodium benzoate, sodium acetate, sodium chloride, leucine and polyethylene glycol. Suitable disintegrators can include, without limitation, starch, methylcellulose, agar, bentonite, cellulose, wood products, alginic acid, guar gum, citrus pulp, carboxymethylcellulose and sodium lauryl sulfate. If desired, a conventional pharmaceutically acceptable dye can be incorporated into the dosage unit form, i.e., any of the standard FD and C dyes. Sweetening and flavoring agents and preservatives can also be included, particularly when a liquid dosage form is formulated, e.g., an elixir, suspension or syrup. Also, when the dosage form is a capsule, it may contain, in addition to materials of the above type, a liquid carrier such as a fatty oil. Various other materials may be present as coatings or to otherwise modify the physical form of the dosage unit. For instance, tablets, pills, or capsules may be coated with shellac, sugar or both. Such compositions should preferably contain at least 0.1% of active components; generally, the active ingredients will be between about 2% to about 90% of the weight of the unit.

The composition of the present invention may also be formulated for intramuscular, subcutaneous, rectal, dermal or topical use by known methods. For those skilled in the art, reference once again is made to the text entitled, "Remington's Pharmaceutical Sciences".

The expression "cholinergic deficit states" applies to both the central nervous system and the peripheral nervous system and covers a wide range of disease states which are well known in the art. Such diseases include Alzheimer's disease, Myasthenia gravis, Huntington's chorea, tardive dyskinesia, dementia associated with Down's syndrome, Parkinson's disease or other drug-induced cholinergic deficit states.

A substantial relief of symptoms from central nervous system cholinergic deficit states may be obtained including those characterized by diminished choline acetyltransferase activity in the central nervous system due to disease or drug intoxication in mammals, especially humans, and intoxication with a competitive antagonist to the action of naturally-occurring central nervous system acetylcholine in mammals, such as atropine, scopolamine, tricyclic antidepressants, anti-Parkinson drugs and certain cardiac anti-arrhythmic agents.

Alzheimer's disease is an example of a naturally occurring central nervous system cholinergic deficit state. The monoacridine derivatives are useful in the treatment of all stages of Alzheimer's disease.

Myasthenia gravis, a peripheral cholinergic deficit state, is a rare neuromuscular disease, with a prevalence rate of 5 to 100 per million population, characterized by weakness and marked fatigability of skeletal muscle. The biochemical defect of this illness is felt to be a decrease in post-synaptic membrane cholinergic receptors. Myasthenia gravis is responsive to anti-cholinesterase treatment. Current treatments include the use of reversible carbamate inhibitors, which typically require dosing of four to twelve times a day. Only one long-acting agent, sustained-release pyridostigmine is available for treatment of this condition. Its clinical duration of action is 6 to 8 hours and its use is markedly curtailed, due to the high frequency of toxicity. Advantages of using monoamine acridines such as 1,2,3,4-tetrahydro-5-aminoacridine or derivatives thereof include a greater safety (lower toxicity), and a longer duration of action (may be administered approximately every eight to twelve hours or longer when administered orally).

The monoamine acridine derivatives, such as 1,2,3,4-tetrahydro-5-aminoacridine, are preferred over the standard reversible carbamate inhibitors, such as physostigmine and are better suited for long term treatment of cholinergic deficit states. Thus, the monoamine acridine derivatives result in greater improvement of symptoms of cholinergic deficit states with fewer side effects.

Furthermore, it appears as though, in addition to having anticholinesterase activity, the monoacridine derivatives have potassium channel blocking properties. Thus, 5-aminoacridine derivatives appear to have a unique mechanism of action; they appear to function both as physostigmine-like compounds and as 4-aminopyridine-like compounds, while having a lower toxicity than either compound taken alone.

The following examples illustrate the present invention and will enable others skilled in the art to understand the invention more completely, and are not intended to be limitative.

EXAMPLE 1

This example describes the use of 1,2,3,4-tetrahydro-5-aminoacridine to treat patients with Alzheimer's disease.

1,2,3,4-tetrahydro-5-aminoacridine was administered to 16 patients with dementia. It was later determined that 12 of the 16 subjects had Alzheimer's disease. All twelve of these patients showed significant improvement with 1,2,3,4-tetrahydro-5-aminoacridine. Four subjects who were believed not to have Alzheimer's disease, or any other central nervous system cholinergic deficit state, also received 1,2,3,4-tetrahydro-5-aminoacridine but did not show any improvement.

The administration of 1,2,3,4-tetrahydro-5-aminoacridine was divided into three phases. In Phase I, oral 1,2,3,4-tetrahydro-5-aminoacridine was administered in increasing doses from 25 mg/day to 200 mg/day over 7-10 days until either clinical response was observed or until a minimum of 150 mg/day of 1,2,3,4-tetrahydro-5-aminoacridine was given for two days without any response. During this phase, complete diagnostic evaluation and psychometric screening for other causes of dementia were conducted.

Patients who showed improvement by psychometric tests in Phase I were started on Phase II, which was a double-blind placebo cross-over design. Two subjects who showed improvement, however, were dropped from the study. One subject was assigned by the conservator to a nursing home. The other subject was dropped from the study because the care-giver was too unreliable to participate in a research study. The ten remaining patients were randomly assigned to placebo or 1,2,3,4-tetrahydro-5-aminoacridine treatment groups. Psychologic assessment was independently done by a physician or psychologist who did not know which drug was assigned. Four weeks later, the subjects received the alternate medication (those on placebo were switched to 1,2,3,4-tetrahydro-5-aminoacridine and vice-versa). Ten patients of the initial sixteen were started on Phase II, and all ten continued to show improvement using 1,2,3,4-tetrahydro-5-aminoacridine in comparison with either their condition before treatment or with the placebo.

The results of the Phase II study are presented in FIGS. 2-5. A single asterisk indicates $p < 0.05$ and a double asterisk indicates $p < 0.001$.

Figure 2:
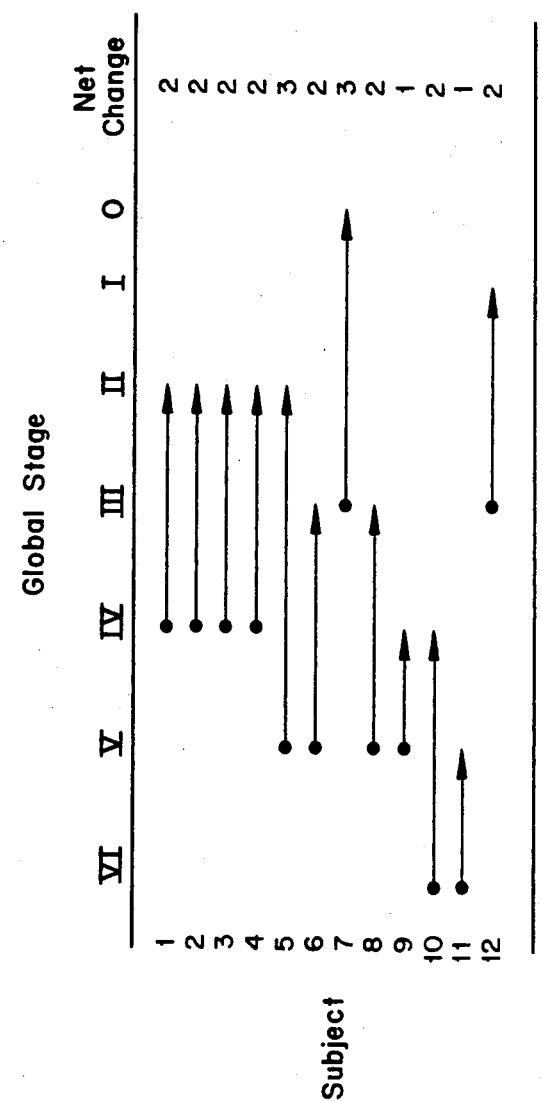
FIG. 2 shows the effect of the administration of oral 1,2,3,4-tetrahydro-5-aminoacridine on the global rating of human subjects with Alzheimer's disease.

FIG. 2 shows the effect of oral 1,2,3,4-tetrahydro-5-aminoacridine on the global rating of the twelve subjects with Alzheimer's disease. Global stages of Alzheimer's disease vary from Stage I which is detectable only by sophisticated psychometric testing to Stage IV where the patient is bedridden, incontinent, agitated, or mute (See Summers, W. K. et al, "Use of THA in Treatment of Alzheimer-Like Dementia", *Biological Psychiatry* (1981), vol. 16, no. 2, pp. 145-153). The top horizontal column gives global stages. The left vertical column identifies each subject. The change for each subject is shown by the respective arrows. Net change represents the improvement in number of global stages. FIG. 2 indicates that patients with Alzheimer's disease can be improved approximately two global stages by the oral administration of 1,2,3,4-tetrahydro-5-aminoacridine regardless of the initial global stage.

Figure 3:
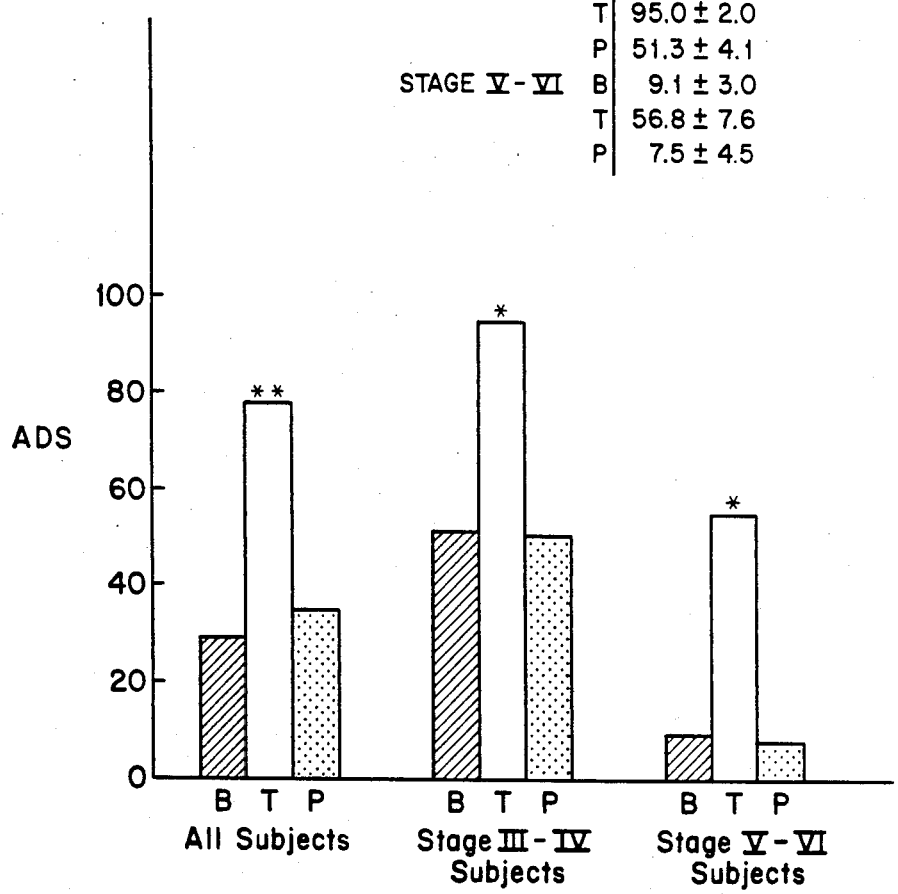
FIG. 3 shows the effect of oral 1,2,3,4-tetrahydro-5-aminoacridine in optimal dose (T) on the Alzheimer's Deficit Scale (ADS). Baseline (B) and placebo (P) data are also shown. A breakdown is also presented for patients with moderately severe Alzheimer's disease (stage 3-4) and patients with severe Alzheimer's disease (stage 5-6).

FIG. 3 shows the effect of oral 1,2,3,4-tetrahydro-5-aminoacridine in optimal dose on the Alzheimer's deficit scale (ADS). The ADS is a 0 (worst) to 100 (best) scale, which spans the full scope of the natural history of Alzheimer's disease. The ADS is a more precise Global Scale than the staging in FIG. 2. Values are given for baseline (condition before treatment) (B), treatment with 1,2,3,4-tetrahydro-5-aminoacridine (T) and treatment with placebo (P). Oral administration of 1,2,3,4-tetrahydro-5-aminoacridine resulted in a 49.1% increase (from 29.3% to 78.4%) in ADS for all subjects, a 43% increase for subjects whose treatment began at stages III-IV, and a 47.7% increase for subjects whose treatment began at stages V-VI.

Figure 4:
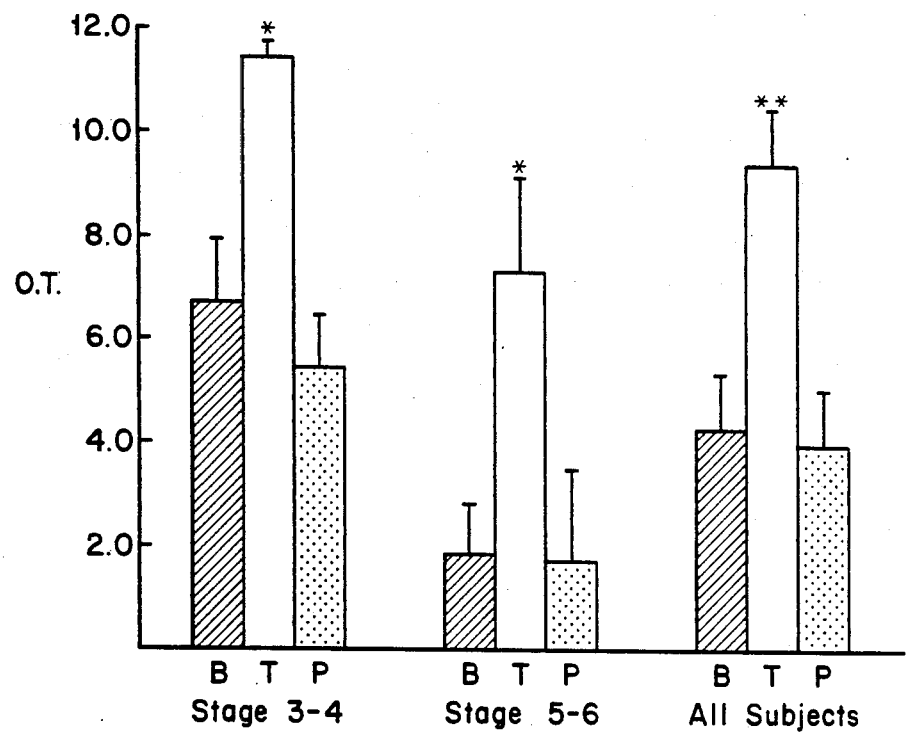
FIG. 4 shows the effect of the administration of oral 1,2,3,4-tetrahydro-5-aminoacridine to patients with Alzheimer's disease on the Orientation Test. Baseline (B) and placebo (P) data are shown. Data is displayed for all patients, patients having moderately severe Alzheimer's disease (stage 3-4) and patients having severe Alzheimer's disease (stage 5-6).

FIG. 4 shows the effect of the oral administration of THA on the Orientation Test (O.T.). The orientation test is a 12-part memory test which subjects in Stages I-V participate in at some level. The Orientation Test evaluates common changeable knowledge. The questions involve recognition of the day, date, month, year, time, precise place, the floor number of the building, where the patient was last seen, an earlier topic of discussion, an item of recent news, the patient's name, and the investigator's name. A full point, half point or no point was assigned to the patient's response to each question. Stage V subjects rarely score above 1 on this test. Data is displayed in FIG. 4 for condition before treatment (B), treatment with 1,2,3,4-tetrahydro-5-aminoacridine (T), and treatment with placebo (P). A further division of the data into results of six Stage I-IV subjects and four Stage V-VI subjects is given.

Figure 5:
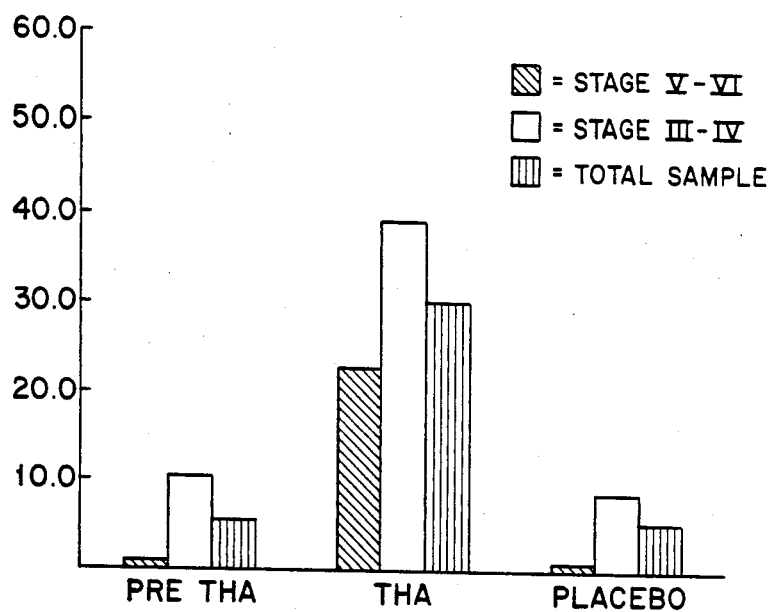
FIG. 5 shows the effect of the administration of oral 1,2,3,4-tetrahydro-5-aminoacridine to patients with Alzheimer's disease on the Names Learning Test.

FIG. 5 shows the effect of the oral administration of 1,2,3,4-tetrahydro-5-aminoacridine on the Names Learning Test (NLT). The NLT is a 12-paired word-association memory test, repeated for up to five trials, for a maximum score of 60. Stage IV-VI subjects frequently cannot participate in this more complex test. Data is displayed for condition before treatment (B), treatment with 1,2,3,4-tetrahydro-5-aminoacridine (T), and treatment with placebo (P) using Wilcox methodology. Further division of the data into results of six Stage III-IV subjects and four Stage V-VI subjects is presented.

Phase III study of oral 1,2,3,4-tetrahydro-5-aminoacridine was offered to any subject showing improvment in Phase II on oral 1,2,3,4-tetrahydro-5-aminoacridine as opposed to placebo. All ten subjects who participated in Phase II continued into Phase III. Because of caution by investigators, the first subject was on THA for 6 months before a second subject was started on Phase I of the protocols. The first subject was on 1,2,3,4-tetrahydro-5-aminoacridine (THA) for 25 months and began to show minimal signs of deterioration from THA-induced remission of Alzheimer's disease in the 18th month of therapy. All other subjects were stable and improved over a mean duration of 10.8 months of therapy.

Toxicology studies were extensive in the study population and consisted of weekly evaluations in Phase I and Phase II and monthly evaluations during Phase III. Parameters studied were electrocardiogram, complete blood count, reticulocyte count, Chemistry-18 panel, and serum THA levels. To date, the only apparent difficulty with using 1,2,3,4-tetrahydro-5-aminoacridine was an apparent increase in 1,2,3,4-tetrahydro-5-aminoacridine absorption by one subject during a gastrointestinal flu episode.

The data provided shows 1,2,3,4-tetrahydro-5-aminoacridine to be significantly effective in reversing symptoms of Alzheimer's disease, principally in memory deficits caused by this illness. Additionally, reversals of gait disturbance, incontinence, and neurological soft signs characteristic of Alzheimer's disease have been noted.

It is recommended that monitoring should be done for signs of minor cholinergic toxicity (minor toxicity includes nausea, sweating, emesis, excessive urination, diarrhea, and excessive nasal discharge).

Figure 6:
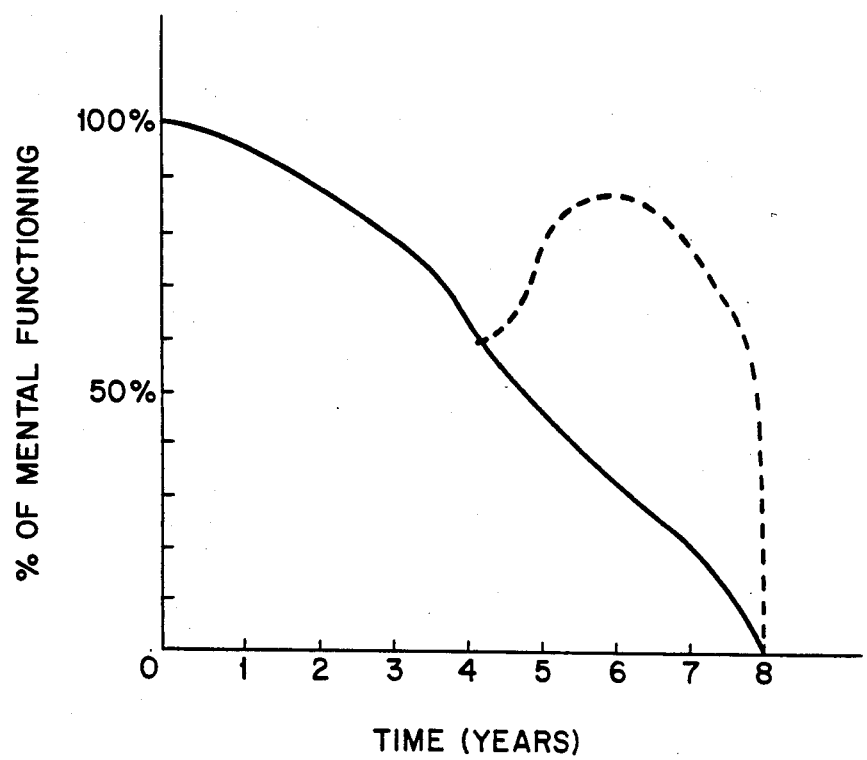
FIG. 6 shows the expected long-term effect of the oral administration of 1,2,3,4-tetrahydro-5-aminoacridine for a hypothetical patient with Alzheimer's disease who is diagnosed in the fourth year of illness and dies in the eighth year of illness.

It has been speculated that 1,2,3,4-tetrahydro-5-aminoacridine is less effective in reversing symptoms of Alzheimer's disease as the illness progresses. FIG. 6 shows the expected long-term effect of 1,2,3,4-tetrahydro-5-aminoacridine on an Alzheimer's disease subject who progresses to Stage III before diagnosis and treatment with 1,2,3,4-tetrahydro-5-aminoacridine. When treatment is started at a deficit level of about 60%, there is approximately a 25% reversal of the deficit. This is followed by a stabilization of the deficit and then a gradual decline over time. The last period is predicted to be a sudden drop. Thus, 1,2,3,4-tetrahydro-5-aminoacridine is expected to be a palliative treatment. The bold line in FIG. 6 depicts the expected course of untreated Alzheimer's disease. The broken line gives the expected effect of 1,2,3,4-tetrahydro-5-aminoacridine on the progression of Alzheimer's disease.

EXAMPLE 2

A 72 year-old white male with a compromised central nervous system function, due to poorly-controlled cardiac arrhythmias and multi-infarct dementia was receiving quinidine 300 mg three times a day. The quinidine resulted in a clouded sensorium but needed to be administered as an anti-arrhythmic. 1,2,3,4-Tetrahydro-5-aminoacridine 25 mg orally four times per day was added to his drug regimen, allowing a higher dosage of the quinidine, with clearer cognitive function. No adverse cardiac effects were noted with the introduction of 1,2,3,4-tetrahydro-5-aminoacridine.

EXAMPLE 3

A 68 year-old white male with known Parkinson's disease complicated by dementia had a dexamethasone suppression test positive, clinically relevant depression. The patient was unable to tolerate greater than three tablets of Sinemet 10/100 per day without marked confusion. The addition of oral 1,2,3,4-tetrahydro-5-aminoacridine 50 mg four times a day in therapeutic dosages allowed stabilization of the Parkinsonian symptoms by means of a higher dose of Sinemet (25/100 four times a day) and the addition of amantadine 100 mg two times a day. The patient was then able to tolerate standard anti-depressant therapy. Further, the addition of anti-depressant therapy and the 1,2,3,4-tetrahydro-5-aminoacridine resulted in a mental capacity which was markedly improved.

From the foregoing description, one of ordinary skill in the art can easily ascertain the essential characteristics of the instant invention, and without departing from the spirit and scope thereof, can make various changes and/or modifications to the invention to adapt it to various usages and conditions. As such, these changes and/or modifications are properly, equitably and intended to be, within the full range of equivalents of the following claims.

What is claimed is:

1. A method of treating a central nervous system or peripheral nervous system cholinergic deficit state in a mammalian organism in need of such treatment, said method comprising administering to said mammal an amount of a monoamine acridine derivative effective in the treatment of a cholinergic deficit state and for a time sufficient to achieve a suitable blood level to treat said cholinergic deficit state, said monoamine acridine derivative having the formula:

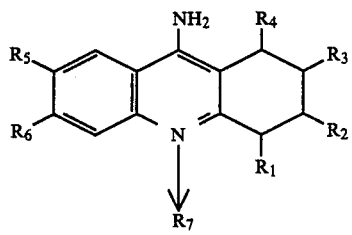

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom; a $C_1$–$C_{20}$ alkyl radical or a radical selected from the group consisting of

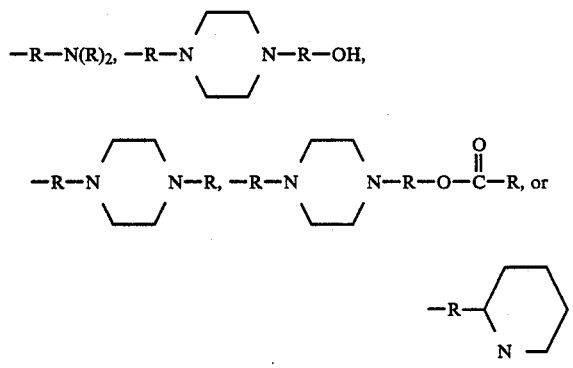

wherein each R is independently selected from $C_1$–$C_{20}$ alkyl; and pharmaceutically acceptable salts thereof.

2. The method as defined by claim 1, wherein said monoamine acridine derivative is administered orally, intramuscularly, subcutaneously, rectally or topically.

3. The method as defined by claim 2, wherein said monoamine acridine derivative is administered orally.

4. The method as defined by claim 1, wherein said monoamine acridine derivative is 1,2,3,4-tetrahydro-5-aminoacridine.

5. The method as defined by claim 1, wherein $R_7$ is selected from the group consisting of

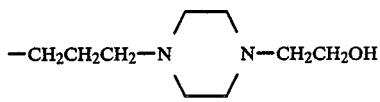
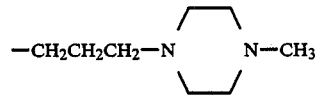
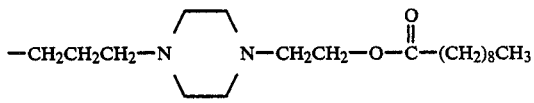
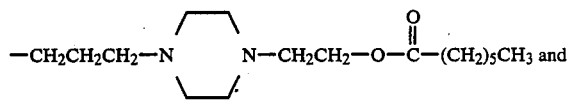
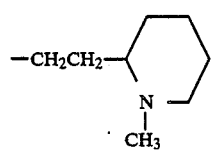

6. The method as defined by claim 1, wherein said central nervous system or peripheral nervous system cholinergic deficit state is Alzheimer's disease, Myasthenia gravis, Huntington's chorea, tardive dyskinesia, dementia associated with Down's syndrome or Parkinson's disease.

7. The method as defined by claim 6, wherein said central nervous system cholinergic deficit state is Alzheimer's disease.

8. The method as defined by claim 1, comprising administering from about 40 mg to about 1 gram of said monoamine acridine derivative per 24 hours.

9. The method as defined by claim 8, comprising administering from about 100 mg to about 300 mg of said monoamine acridine derivative per 24 hours.

10. The method as defined by claim 1, said monoamine acridine derivative further including a pharmaceutically acceptable inert carrier therefor.

11. A method of treating Alzheimer's disease in a mammal, said method comprising administering to said mammal about 100 mg to about 300 mg per 24 hours of 1,2,3,4-tetrahydro-5-aminoacridine and a pharmaceutically acceptable inert carrier therefor.

12. A method of maintaining a blood level of about 5 µg to about 70 µg of a monoamine acridine derivative having the formula:

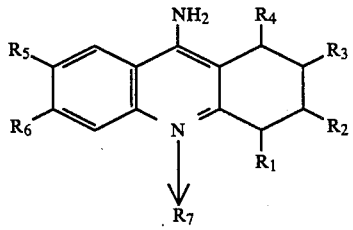

wherein $R_1$ represents hydrogen, hydroxy, methyl, methoxy, ethyl or ethoxy; and $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom; a $C_1$–$C_{20}$ alkyl radical or a radical selected from the group consisting of

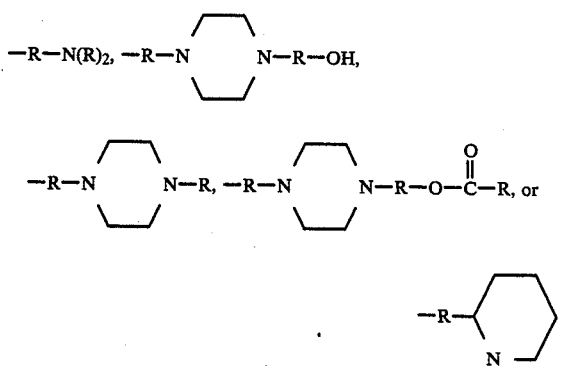

wherein each R is independently selected from $C_1$–$C_{20}$ alkyl; and pharmaceutically acceptable salts thereof, in a mammalian organism having a central nervous system or peripheral nervous system cholinergic deficit state, comprising administering to said mammalian organism from about 40 mg to about 1 gram of said monoamine acridine derivative.

13. A method of treating central nervous system or peripheral nervous system cholinergic deficit states in a mammalian organism in need of such treatment, said method comprising orally administering to said mammal an amount of a monoamine acridine derivative effective in the treatment of cholinergic deficit states and for a time sufficient to achieve a suitable blood level to treat said cholinergic deficit state, said monoamine acridine derivative having the formula:

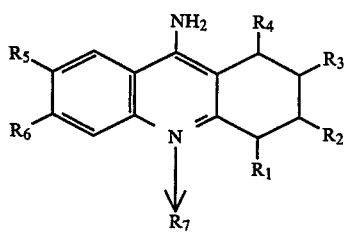

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom and pharmaceutically acceptable salts thereof.

14. The method as defined by claim 13, wherein said monoamine acridine derivative is 1,2,3,4-tetrahydro-5-aminoacridine.

15. The method as defined by claim 13, wherein said central nervous system or peripheral nervous system cholinergic deficit state is Alzheimer's disease, Myasthenia gravis, Huntington's chorea, tardive dyskinesia, dementia associated with Down's syndrome or Parkinson's disease.

16. The method as defined by claim 15, wherein said central nervous system cholinergic deficit state is Alzheimer's disease.

17. The method as defined by claim 13, comprising administering from about 40 mg to about 1 gram of said monoamine acridine derivative per 24 hours.

18. The method as defined by claim 17, comprising administering from about 100 mg to about 300 mg of said monoamine acridine derivative per 24 hours.

19. The method as defined by claim 18, comprising administering from about 100 mg to about 200 mg of said monoamine acridine derivative per 24 hours.

20. The method as defined by claim 13, said monoamine acridine derivative further including a pharmaceutically acceptable inert carrier therefor.

21. A pharmaceutical composition of matter for treating central nervous system or peripheral nervous system cholinergic deficit states in a mammalian organism in need of such treatment, said composition comprising a unit dosage amount of a monoamine acridine derivative having the formula:

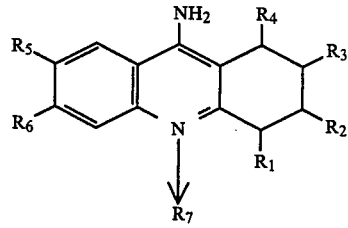

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$, and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom; a $C_1$–$C_{20}$ alkyl radical or a radical selected from the group consisting of

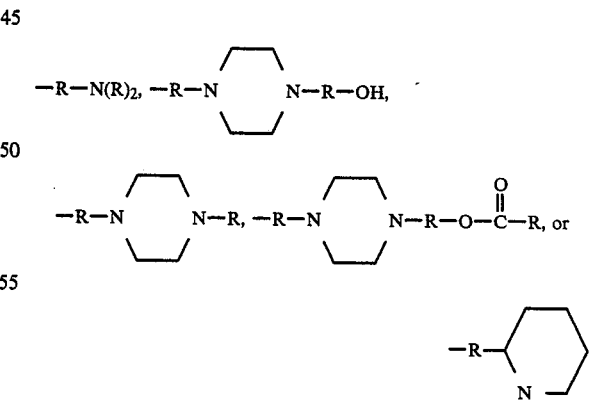

wherein each R is independently selected from $C_1$–$C_{20}$ alkyl; and pharmaceutically acceptable salts thereof in an amount sufficient to treat said central nervous system or peripheral nervous system cholinergic deficit state and a pharmaceutically acceptable inert carrier therefor, with the provisos that (i) if $R_1$, $R_2$, $R_3$, $R_4$, $R_5$ and $R_6$ are each hydrogen, then $R_7$ cannot be without a substituent, (ii) if $R_1$ and $R_2$ together form a double bond, $R_3$ and $R_4$ together form a double bond and $R_5$ and $R_6$ are each hydrogen, then $R_7$ cannot be without a substituent, and (iii) if $R_3$ and $R_4$ together form a double bond and $R_7$ is without a substituent then $R_1$ cannot be a hydrogen atom.

22. The pharmaceutical composition of matter as defined by claim 21, said pharmaceutical composition of matter being suitable for oral, intramuscular, subcutaneous, rectal or topical administration.

23. The pharmaceutical composition of matter as defined by claim 22, said pharmaceutical composition of matter being suitable for oral administration.

24. The pharmaceutical composition of matter as defined by claim 21, wherein said central nervous system or peripheral nervous system cholinergic deficit state is Alzheimer's disease, Myasthenia gravis, Huntington's chorea, tardive dyskinesia, dementia associated with Down's syndrome or Parkinson's disease.

25. The pharmaceutical composition of matter as defined by claim 24, wherein said central nervous system cholinergic deficit state is Alzheimer's disease.

26. The pharmaceutical composition of matter as defined by claim 21, comprising from about 40 mg to about 1 gram of said monoamine acridine derivative.

27. The pharmaceutical composition of matter as defined by claim 26, comprising from about 100 mg to about 300 mg of said monoamine acridine derivative.

28. A compound having the formula

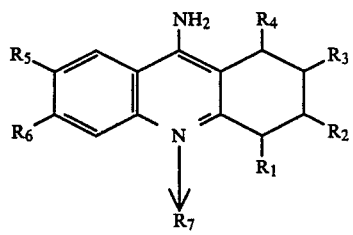

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ represents a $C_1$-$C_{20}$ alkyl radical or a radical selected from the group consisting of

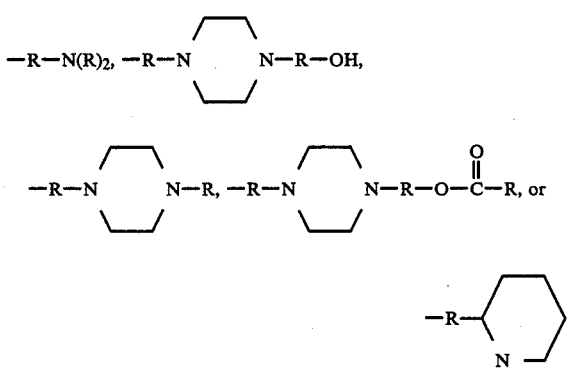

wherein each R is independently selected from $C_1$-$C_{20}$ alkyl.

29. The compound as defined by claim 28, wherein $R_1$, $R_2$, $R_3$, $R_4$, $R_5$ and $R_6$ are hydrogen and $R_7$ is selected from the group consisting of

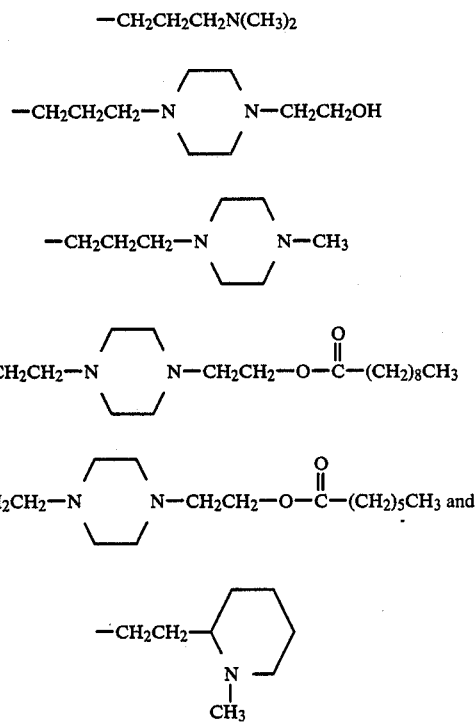

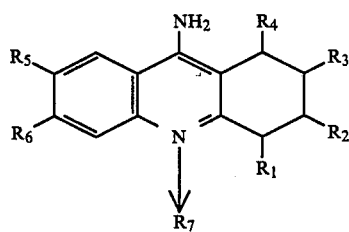

30. A pharmaceutical composition of matter for treating central nervous system or peripheral nervous system cholinergic deficit states in a mammalian organism in need of such treatment, said composition comprising a unit dosage amount of a monoamine acridine derivative having the formula:

wherein $R_1$ represents hydrogen, hydroxy, methyl, methoxy, ethyl or ethoxy; $R_1$ and $R_2$ together may form a double bond, $R_3$ and $R_4$ together form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom and pharmaceutically acceptable salts thereof in an amount sufficient to treat said central nervous system or peripheral nervous system cholinergic deficit state and a pharmaceutically acceptable inert carrier therefor, with the provisos that (i) if $R_1$, $R_2$, $R_3$, $R_4$, $R_5$ and $R_6$ are each hydrogen then $R_7$ cannot be without a substituent, (ii) if $R_1$ and $R_2$ together form a double bond, $R_3$ and $R_4$ together form a double bond and $R_5$ and $R_6$ are each hydrogen, then $R_7$ cannot be without a substituent, and (iii) if $R_3$ and $R_4$ together form a double bond and $R_7$ is without a substituent then $R_1$ cannot be a hydrogen atom.

31. The pharmaceutical composition of matter as defined by claim 30, wherein said central nervous system or peripheral nervous system cholinergic deficit state is Alzheimer's disease, Myasthenia gravis, Huntington's chorea, tardive dyskinesia, dementia associated with Down's syndrome or Parkinson's disease.

32. The pharmaceutical composition of matter as defined by claim 31, wherein said central nervous system cholinergic deficit state is Alzheimer's disease.

33. The pharmaceutical composition of matter as defined by claim 30, comprising from about 40 mg to about 1 gram of said monoamine acridine derivative.

34. The pharmaceutical composition of matter as defined by claim 33, comprising from about 100 mg to about 300 mg of said monoamine acridine derivative.

35. The pharmaceutical composition of matter as defined by claim 34, comprising from about 100 mg to about 200 mg of said monoamine acridine derivative.

36. A compound having the formula

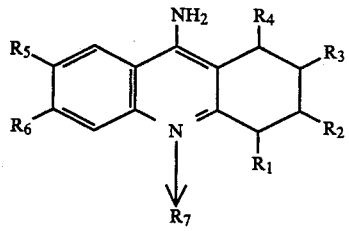

wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ represents an oxygen atom, with the provisos that (i) if $R_1$, $R_2$, $R_3$, $R_4$, $R_5$ and $R_6$ are each hydrogen, then $R_7$ cannot be without a substituent, (ii) if $R_1$ and $R_2$ together form a double bond, $R_3$ and $R_4$ together form a double bond and $R_5$ and $R_6$ are each hydrogen, then $R_7$ cannot be without a substituent, and (iii) if $R_3$ and $R_4$ together form a double bond and $R_7$ is without a substituent then $R_1$ cannot be a hydrogen atom.

37. The pharmaceutical composition of matter as defined by claim 21, wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ is without a substituent or $R_7$ is an oxygen atom or a radical selected from the group consisting of

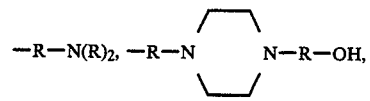

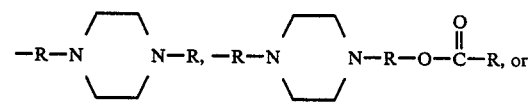

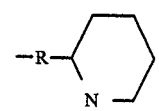

wherein each R is independently selected from $C_1$-$C_{20}$ alkyl; and pharmaceutically acceptable salts thereof in an amount sufficient to treat said central nervous system or peripheral nervous system cholinergic deficit state and a pharmaceutically acceptable inert carrier therefor with the provisos that (i) if $R_1$, $R_2$, $R_3$, $R_4$, $R_5$ and $R_6$ are each hydrogen then $R_7$ cannot be without a substituent, (ii) if $R_1$ and $R_2$ together form a double bond, $R_3$ and $R_4$ together form a double bond and $R_5$ and $R_6$ are each hydrogen, then $R_7$ cannot be without a substituent, and (iii) if $R_3$ and $R_4$ together form a double bond and $R_7$ is without a substituent then $R_1$ cannot be hydrogen.

38. The compound as defined by claim 28, wherein $R_1$ represents hydrogen, hydroxy, methyl, methoxy, ethyl or ethoxy; $R_1$ and $R_2$ together may form a double bond, $R_3$ and $R_4$ together may form a double bond, or $R_1$, $R_2$, $R_3$ and $R_4$ are all hydrogen; $R_5$ represents hydrogen, hydroxy, methoxy or ethoxy; $R_6$ represents hydrogen, hydroxy, methoxy or ethoxy; and $R_7$ represents a radical selected from the group consisting of

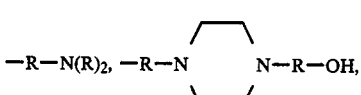

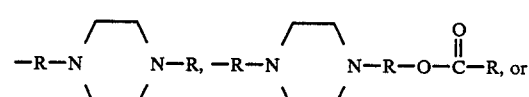

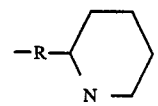

wherein each R is independently selected from $C_1$-$C_{20}$ alkyl.

* * * * *

UNITED STATES PATENT AND TRADEMARK OFFICE

CERTIFICATE EXTENDING PATENT TERM
UNDER 35 U.S.C. § 156

PATENT NO.      : 4,816,456

ISSUED          : March 28, 1989

INVENTOR(S)     : William K. Summers

PATENT OWNER    : William K. Summers

This is to certify that there has been presented to the

COMMISSIONER OF PATENTS AND TRADEMARKS an application under 35 U.S.C. § 156 for an extension of the patent term. Since it appears that the requirements of the law have been met, this certificate extends the term of the patent for the period of 343 days from October 1, 2006, the original expiration date of the patent, with all rights pertaining thereto as provided by 35 U.S.C. § 156(b).

I have caused the seal of the Patent and Trademark Office to be affixed this 20th day of November 1997.

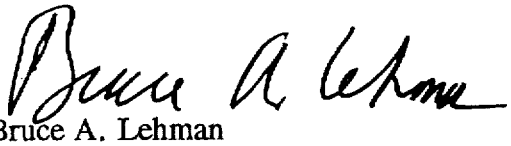

Bruce A. Lehman
Assistant Secretary of Commerce and
  Commissioner of Patents and Trademarks